(12) United States Patent
Sun et al.

(10) Patent No.: US 7,952,348 B2
(45) Date of Patent: May 31, 2011

(54) FLEXIBLE EDDY CURRENT ARRAY PROBE AND METHODS OF ASSEMBLING THE SAME

(75) Inventors: Haiyan Sun, Niskayuna, NY (US); Yuri Plotnikov, Niskayuna, NY (US); Changting Wang, Niskayuna, NY (US); William Stewart McKnight, Hamilton, OH (US); Ui Suh, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 353 days.

(21) Appl. No.: 11/935,077

(22) Filed: Nov. 5, 2007

(65) Prior Publication Data

US 2009/0115411 A1 May 7, 2009

(51) Int. Cl.
*G01N 27/82* (2006.01)
*G01R 33/12* (2006.01)

(52) U.S. Cl. ......... 324/240; 324/234; 324/238; 324/239

(58) Field of Classification Search .................. 324/228, 324/234, 235, 236, 237, 238, 239, 240, 242, 324/243

See application file for complete search history.

(56) References Cited

U.S. PATENT DOCUMENTS

| | | | |
|---|---|---|---|
| 4,310,821 A | 1/1982 | Frances | |
| 4,651,093 A * | 3/1987 | Detriche et al. | 324/232 |
| 4,706,020 A | 11/1987 | Viertl et al. | |
| 5,006,800 A | 4/1991 | Hedengren et al. | |
| 5,182,513 A | 1/1993 | Young et al. | |
| 5,237,271 A | 8/1993 | Hedengren | |
| 5,262,722 A * | 11/1993 | Hedengren et al. | 324/242 |
| 5,278,498 A | 1/1994 | Vernon et al. | |
| 5,315,234 A | 5/1994 | Sutton, Jr. et al. | |
| 5,371,461 A | 12/1994 | Hedengren | |
| 5,371,462 A | 12/1994 | Hedengren et al. | |
| 5,389,876 A | 2/1995 | Hedengren et al. | |
| 5,418,457 A | 5/1995 | Hedengren et al. | |
| 5,442,286 A | 8/1995 | Sutton, Jr. et al. | |
| 5,659,248 A | 8/1997 | Hedengren et al. | |
| 5,801,532 A | 9/1998 | Patton et al. | |
| 5,841,277 A | 11/1998 | Hedengren et al. | |
| 5,903,147 A | 5/1999 | Granger, Jr. et al. | |
| 5,966,011 A | 10/1999 | Goldfine et al. | |
| 6,150,809 A | 11/2000 | Tiernan et al. | |
| 6,252,393 B1 | 6/2001 | Hedengren | |
| 6,418,335 B2 * | 7/2002 | Avrin et al. | 600/409 |
| 6,504,363 B1 | 1/2003 | Dogaru et al. | |
| 6,608,478 B1 | 8/2003 | Dziech et al. | |

(Continued)

OTHER PUBLICATIONS

Ditchburn, R.J., et al.; Planar Rectangular Spiral Coils in Eddy-Current Non-Destructive Inspection; NDT&E International; pp. 690-700; vol. 38, Issue 8; Dec. 2005.

*Primary Examiner* — Kenneth J Whittington
(74) *Attorney, Agent, or Firm* — William Scott Andes, Esq.; Armstrong Teasdale LLP

(57) ABSTRACT

A method of assembling an eddy current probe for use in nondestructive testing of a sample is described. The method includes positioning at least one substantially planar spiral drive coil within the eddy current probe, such that the drive coil is at least one of adjacent to and at least partially within a flexible material. The method further includes coupling at least one unpackaged solid-state magnetic field sensor to the at least one drive coil.

14 Claims, 13 Drawing Sheets

U.S. PATENT DOCUMENTS

| | | |
|---|---|---|
| 6,693,425 B2 | 2/2004 | Wache |
| 6,707,297 B2 | 3/2004 | Nath et al. |
| 6,720,775 B2 | 4/2004 | Plotnikov et al. |
| 6,727,691 B2 | 4/2004 | Goldfine et al. |
| 6,784,662 B2 | 8/2004 | Schlicker et al. |
| 6,812,697 B2 | 11/2004 | McKnight et al. |
| 6,822,443 B1 | 11/2004 | Dogaru |
| 6,888,346 B2 | 5/2005 | Wincheski et al. |
| 6,888,347 B2 | 5/2005 | Batzinger et al. |
| 6,911,826 B2 | 6/2005 | Plotnikov et al. |
| 6,933,717 B1 | 8/2005 | Dogaru et al. |
| 6,992,482 B2 | 1/2006 | Shay et al. |
| 7,015,690 B2 | 3/2006 | Wang et al. |
| 7,049,811 B2 | 5/2006 | Schlicker et al. |
| 7,095,224 B2 | 8/2006 | Goldfine et al. |
| 7,106,055 B2 | 9/2006 | Goldfine et al. |
| 7,161,351 B2 | 1/2007 | Goldfine et al. |
| 7,188,532 B2 | 3/2007 | Goldfine et al. |
| 2005/0007108 A1* | 1/2005 | Dogaru ............... 324/235 |
| 2005/0122100 A1* | 6/2005 | Wan et al. ............ 324/247 |
| 2006/0017434 A1 | 1/2006 | Tenley et al. |
| 2006/0023961 A1 | 2/2006 | Suh et al. |
| 2006/0290349 A1 | 12/2006 | Na et al. |
| 2009/0206831 A1* | 8/2009 | Fermon et al. ......... 324/240 |

* cited by examiner

FLEXIBLE EDDY CURRENT ARRAY PROBE AND METHODS OF ASSEMBLING THE SAME

BACKGROUND OF THE INVENTION

This invention relates generally to nondestructive testing, and more particularly to an eddy current array probe and methods of assembling the same.

Eddy current (EC) inspection devices are used to detect abnormal indications in a conductive component being tested such as, but not limited to, gas turbine engine components. For example, known EC inspection devices may be used to detect cracks, pings, dings, raised material, and/or other surface and subsurface imperfections on a surface of the component, and/or to evaluate material properties of the component including the electrical conductivity, density, and/or degrees of heat treatment of the component.

During operation, known EC devices measure the interaction between an electromagnetic field generated by the EC device and the component being tested. For example, at least some known EC devices include a probe coil that generates a magnetic field. When the coil is positioned adjacent to a conductive component, an eddy current is generated on the surface of the component. A flaw on and/or near the surface of the component disrupts the eddy current field causing a secondary field to be produced that is received by the eddy current probe coil or by a sensor coil in the eddy current probe. The secondary field is converted to an electrical signal that may be observed on a monitor or recorded, for example, on a strip chart recorder.

In use, a substantially constant pressure is applied to the probe as the coil moves along the surface of the component being tested. The constant pressure facilitates maintaining an integrity of the signal generated by the EC probe. However, when the EC probe is not oriented substantially normal to the surface of the component being tested, a "lift-off effect" may be created.

To facilitate reducing lift-off-effects, at least one known EC probe includes a dual-coil probe, e.g. a differential probe that includes a pair of coils with an opposite polarity. Each coil in the dual-coil probe generates an electrical signal when the probe contacts a surface of the component being tested. More specifically, when the dual coil probe passes over a smooth surface of the component being tested, the signals cancel each other. However, when the dual coil probe passes over a local physical abnormality on the surface, the probe generates a signal that is proportional to the size, depth, etc., of the physical abnormality.

When a non-continuous component surface feature is inspected, such as a feature on a rotating part, known differential probes may have difficulty testing sharp curvatures, in such areas as corners and cusps. During operation, when such probes encounter a corner or cusp, the differential probe device may become skewed to the surface of the component, such that a resulting lift-off effect may cause a loss of usable data. Accordingly, known EC probes may be less effective in generating an accurate response when the EC probe is used to detect conditions on a component having complex geometries, and/or a component having irregular conditions, such as may be prevalent in components including sharp indexing or objects that extend into the path of the probe such that the probe cannot consistently remain normal to the scan surface. Known EC probes use coils as the sensing element to detect surface flaws. In order to accurately detect small surface flaws, a probe must provide a combination of high sensitivity and high spatial resolution.

BRIEF DESCRIPTION OF THE INVENTION

In one aspect, a method of assembling an eddy current probe for use in nondestructive testing of a sample is described. The method includes positioning at least one substantially planar spiral drive coil within the eddy current probe, such that the drive coil is at least one of adjacent to and at least partially within a flexible material. The method further includes coupling at least one unpackaged solid-state magnetic field sensor to the at least one drive coil.

In another aspect, an eddy current probe is described. The eddy current probe includes at least one substantially planar spiral drive coil including at least one conductive trace positioned at least one of adjacent to and at least partially within a flexible material. The eddy current probe also includes a solid-state magnetic field sensor coupled to the at least one drive coil to form the eddy current probe.

In yet another aspect, a device for inspecting a component is provided. The device includes a plurality of eddy current probes coupled in an array. Each of the plurality of eddy current probes includes at least one substantially planar spiral drive coil including at least one conductive trace positioned at least one of adjacent to and at least partially within a flexible material. Each of the plurality of eddy current probes also includes at least one unpackaged solid-state magnetic field sensor coupled to said at least one planar spiral drive coil.

DETAILED DESCRIPTION OF THE INVENTION

Figure 1:
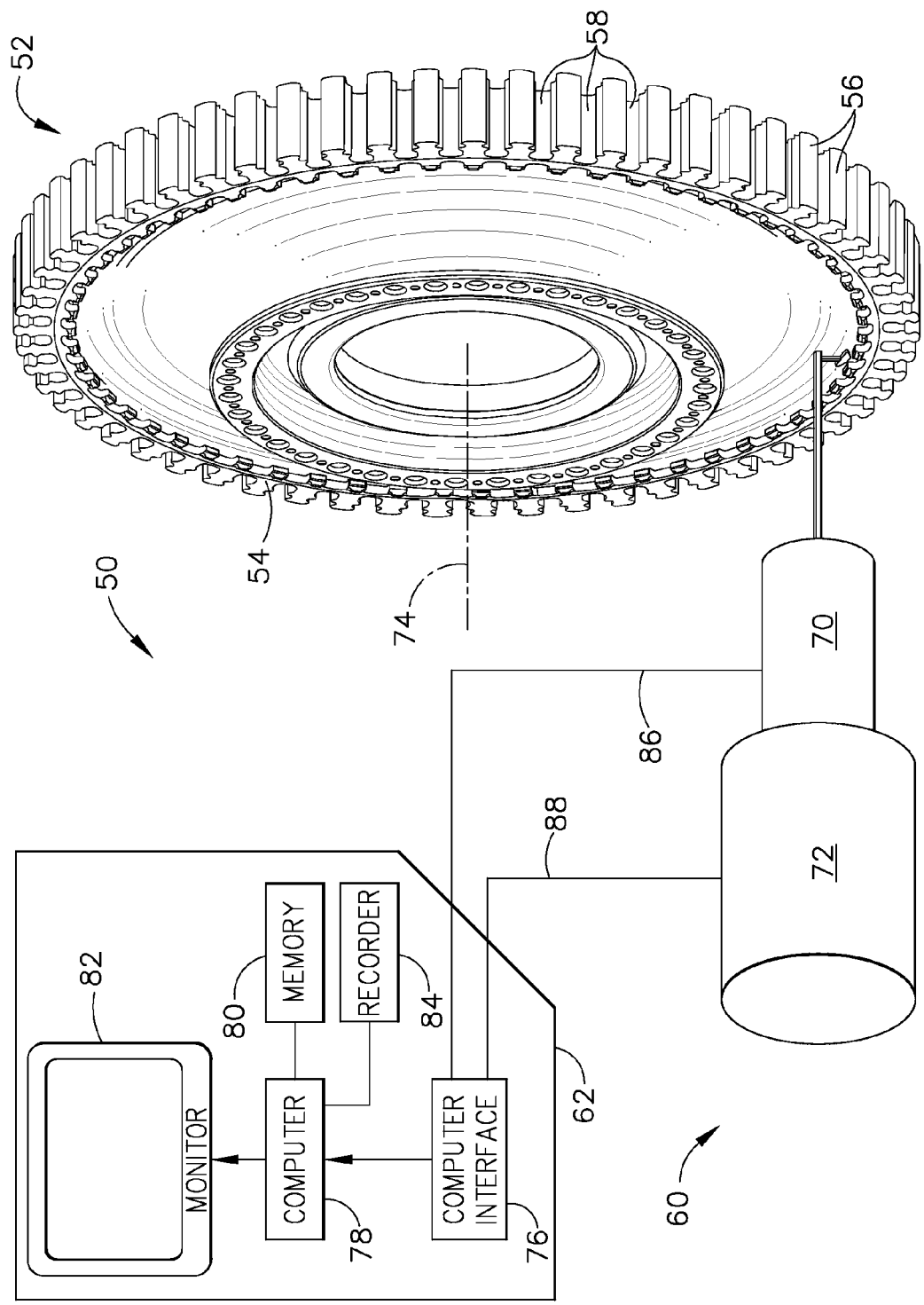
FIG. 1 is a schematic diagram of an exemplary eddy current surface flaw detection system.

As described above, conventional induction eddy current probes use coils as the sensing element to detect surface flaws. In order to accurately detect small surface flaws, a probe must combine high sensitivity and high spatial resolution. To achieve high spatial resolution, a small sensing coil is desired. In order to improve sensitivity, a large number of turns in the coil is desired. However, the total number of turns that can be placed around a coil is limited by the geometrical dimensions of the coil. The tradeoffs between the number of turns and the coil size, sensitivity and spatial resolution, limit the capability of inductive probes to detect small abnormalities.

In contrast to the limited sensitivity of a sensing coil that includes a small number of turns in order to maintain a small size and high spatial resolution, solid-state magnetic field sensors are small, yet provide high sensitivity to small magnetic fields. Examples of solid-state magnetic field sensors are, but are not limited to, a Hall sensor, an anisotropic magnetic resistor (AMR), a giant magnetic resistor (GMR), a tunneling magnetic resistor (TMR), an extraordinary magnetoresistor (EMR), and a giant magnetoimpedance (GMI). Solid-state magnetic field sensors are referred to herein as solid-state sensors. One specific example of a solid-state magnetic field sensor is a spin tunnel junction sensor fabricated by Micro Magnetics of Fall River, Mass.

The sensitivity and resolution of an eddy current probe is determined not only by the sensing element, but also by the excitation coil, also referred to herein as a drive coil, as well as the configuration of the drive coils. Various types of drive coils are used in known eddy current probes, for example, pancake coils and meander coils. Pancake coils are bulky, hard to miniaturize, and difficult to scale into an array. Meander coils have a pair or pairs of conductive lines in parallel with each other and current flows in opposite directions in each pair. Since the induced magnetic field intensity is proportional to the number of turns in the driving coil, the magnetic fields induced by meander coils are weak compared with other coil configuration with multiple turns. In contrast to the above described drive coils, spiral types of coils, such as, but not limited to, coils described in U.S. Pat. No. 5,389,876, can be fabricated within a flexibly conforming structure using High Density Interconnect (HDI) precision processing. Spiral coils can be precision, multi-layer, multi-turn coils that have a small footprint and provide a strong drive field. They can be efficiently fabricated into arrays with substantially identical elements.

The distance from the drive coil and the surface of a test sample, called "lift-off", has to be minimized and maintained constant during inspection in order to maximize probe detection of small abnormalities in the test sample. Often, a pressure is applied to the probe as the coil moves along the surface of the component being tested. The pressure facilitates maintaining a minimum and constant lift-off of the probe. However, when inspecting components with complex geometry, having a curved contoured surface, such as turbine blade, dovetail slots, transition zone in the turbine disks, etc., it is hard to maintain the lift-off. To improve productivity of eddy current inspection, a plurality of elements is arranged onto an array. It is difficult to maintain a constant lift-off across all the elements in the array when inspecting the above-mentioned complex contour objects. In this case, a flexible array probe is necessary. Because of flexibility, the entire array can conform well to the inspected surface and the lift-off of each element in the array probe can be maintained constant.

FIG. 1 is a schematic diagram of an exemplary eddy current flaw detection system 50 that may be used to inspect a component 52 such as, but not limited to, a gas turbine engine disk 54. In the exemplary embodiment, disk 54 includes a plurality of dovetail posts 56 and a plurality of circumferentially-spaced dovetail slots 58 defined between adjacent pairs of posts 56.

Although the methods and apparatus herein are described with respect to posts 56 and dovetail slots 58, it should be appreciated that the methods and apparatus can be applied to a wide variety of components. For example, component 52 may have any operable shape, size, and configuration. Examples of such components may include, but are not limited to, components of gas turbine engines such as seals, flanges, turbine blades, turbine vanes, and/or flanges. The component may be fabricated of any base material such as, but not limited to, nickel-base alloys, cobalt-base alloys, titanium-base alloys, iron-base alloys, and/or aluminum-base alloys. More specifically, although the methods and apparatus herein are described with respect to aircraft engine components, it should be appreciated that the methods and apparatus can be applied to or used to inspect, a wide variety of components used within a steam turbine, a nuclear power plant, an automotive engine, or any other mechanical components.

In the exemplary embodiment, detection system 50 includes a probe assembly 60 and a data acquisition/control system 62. Probe assembly 60 includes an eddy current coil/probe 70 and a probe manipulator 72 that is coupled to probe 70. Eddy current probe 70 and probe manipulator 72 are each electrically coupled to data acquisition/control system 62 such that control/data information can be transmitted to/from eddy current probe 70/probe manipulator 72 and data acquisition/control system 62. In an alternative embodiment, system 50 also includes a turntable (not shown) configured to rotate component 52 around a central axis 74 during the inspection procedure.

Data acquisition/control system 62 includes a computer interface 76, a computer 78, such as a personal computer with a memory 80, and a monitor 82. Computer 78 executes instructions stored in firmware (not shown). Computer 78 is programmed to perform functions described herein, and as used herein, the term "computer" is not limited to just those integrated circuits referred to in the art as computers, but rather broadly refers to computers, processors, microcontrollers, microcomputers, programmable logic controllers, application specific integrated circuits, and other programmable circuits, and these terms are used interchangeably herein.

Memory 80 is intended to represent one or more volatile and/or nonvolatile storage facilities that shall be familiar to those skilled in the art. Examples of such storage facilities often used with computer 78 include, but are not limited to, solid-state memory (e.g., random access memory (RAM), read-only memory (ROM), and flash memory), magnetic storage devices (e.g., floppy disks and hard disks), and/or optical storage devices (e.g., CD-ROM, CD-RW, and DVD). Memory 80 may be internal to or external from computer 78. Data acquisition/control system 62 also includes a recording device 84 such as, but not limited to, a strip chart recorder, a C-scan, and an electronic recorder that is electrically coupled to either computer 78 and/or eddy current probe 70.

In use, a component 52, such as disk 54, is mounted on a fixture (not shown) that secures the component 52 in place during inspection. Eddy current probe 70 is positioned within dovetail slots 58 to facilitate enabling substantially all of the interior of dovetail slots 58 to be scanned during inspection. In the exemplary embodiment, probe manipulator 72 is a six-axis manipulator. Eddy current probe 70 generates electrical signals in response to the eddy currents induced within the surface of dovetail slots 58 during scanning of dovetail slots 58 by probe 70. Electrical signals generated by probe 70 are received by data acquisition/control system 62 via a data communications link 86 and are either stored in memory 80 or recorder 84. Computer 78 is also coupled to probe manipulator 72 by a communications link 88 to facilitate controlling the scanning of disk 54. A keyboard (not shown) is electrically coupled to computer 78 to facilitate operator control of the inspection of disk 54. In the exemplary embodiment, a printer (not shown) may be provided to generate hard copies of the images generated by computer 78.

Figure 2:
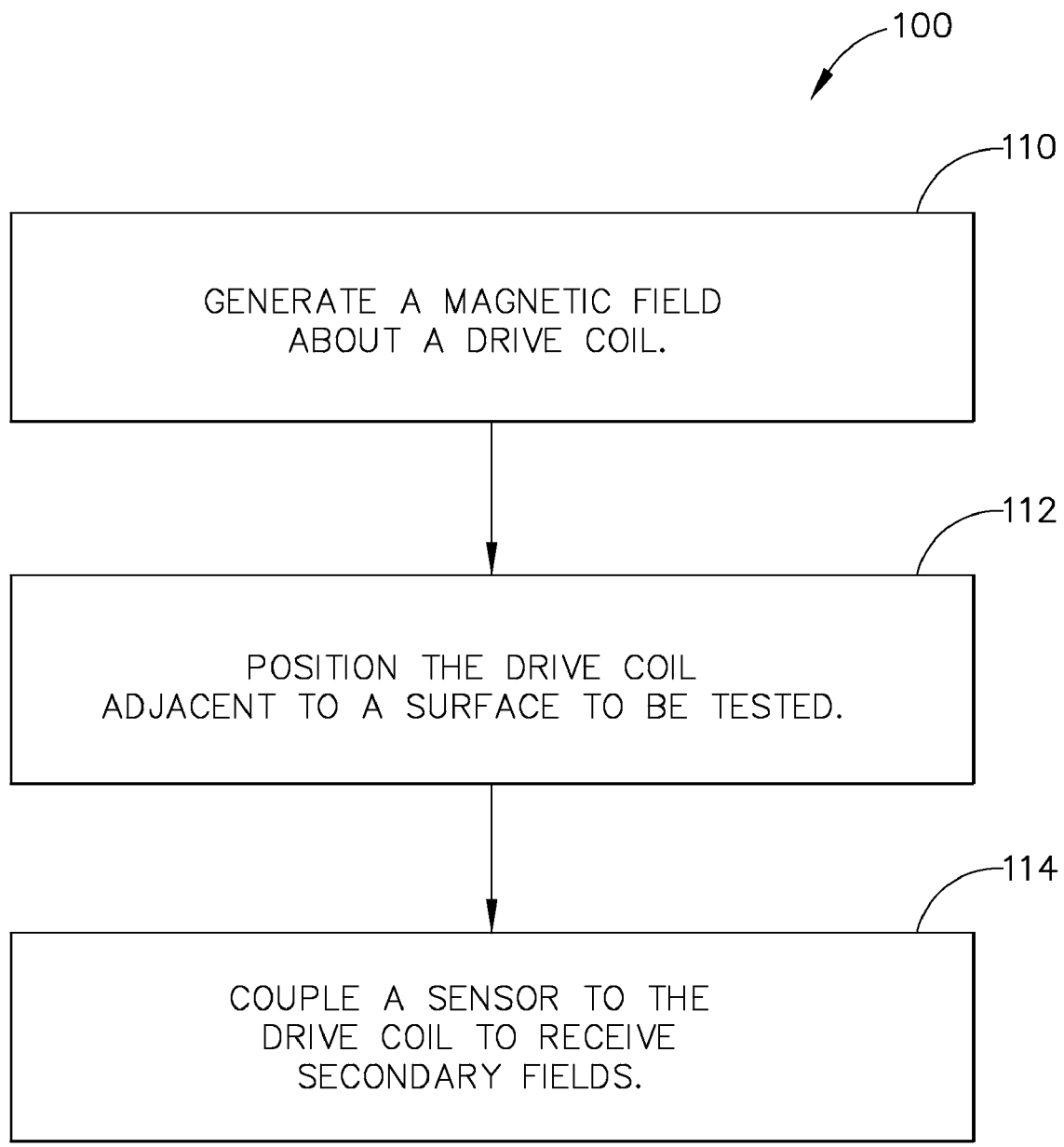
FIG. 2 is a flowchart illustrating an exemplary method for performing an eddy current inspection.

FIG. 2 is an exemplary method 100 for performing an eddy current inspection. The method 100 includes generating 110 a magnetic field about a drive coil. Generating 110 may include, but is not limited to only supplying an alternating current to a drive coil, wherein the drive coil is a planar spiral coil. Method 100 also includes positioning 112 the planar spiral drive coil adjacent to a surface to be tested. In the exemplary embodiment, positioning 112 includes orienting the planar spiral drive coil substantially parallel to the surface to be tested. Such an orientation of the coil causes the magnetic field generated by the drive coil to be oriented normal to the surface being tested.

The method 100 also includes coupling 114 a sensor to the drive coil to receive secondary fields. In the exemplary embodiment, the sensor is an unpackaged solid-state magnetic field sensor that is coupled to a substantially planar spiral drive coil. Secondary fields of interest are received at the sensor after the magnetic fields generated by the drive coil are reflected off a surface flaw on or in the surface being tested. The method 100 may further include configuring the sensor to convert the reflected secondary field into an electric signal that may be viewed and/or recorded.

Figure 3:
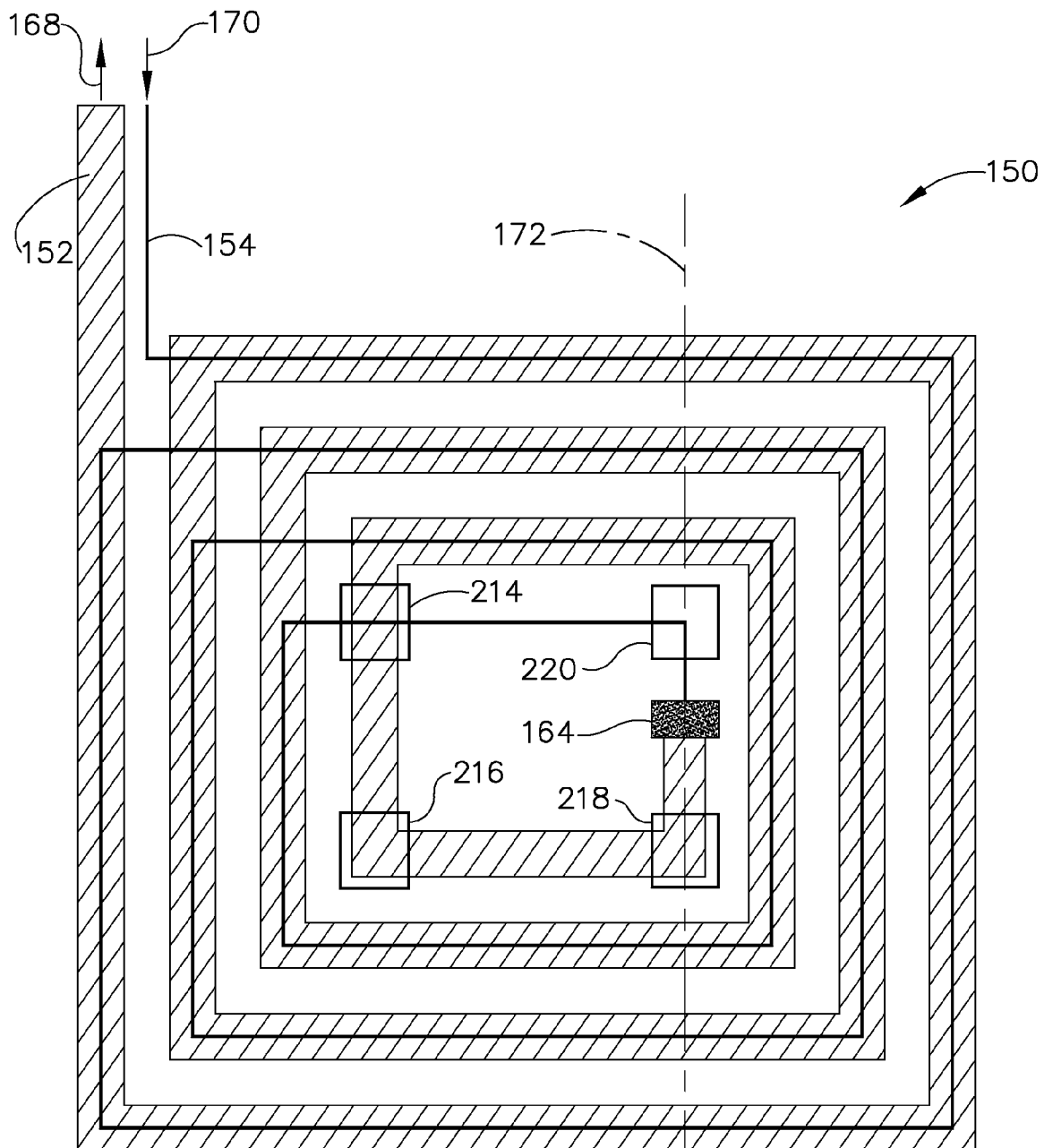
FIG. 3 is a schematic top planar view of a double layer, multi-turn coil comprised of two single layer coil elements including bonding pads.
Figure 4:
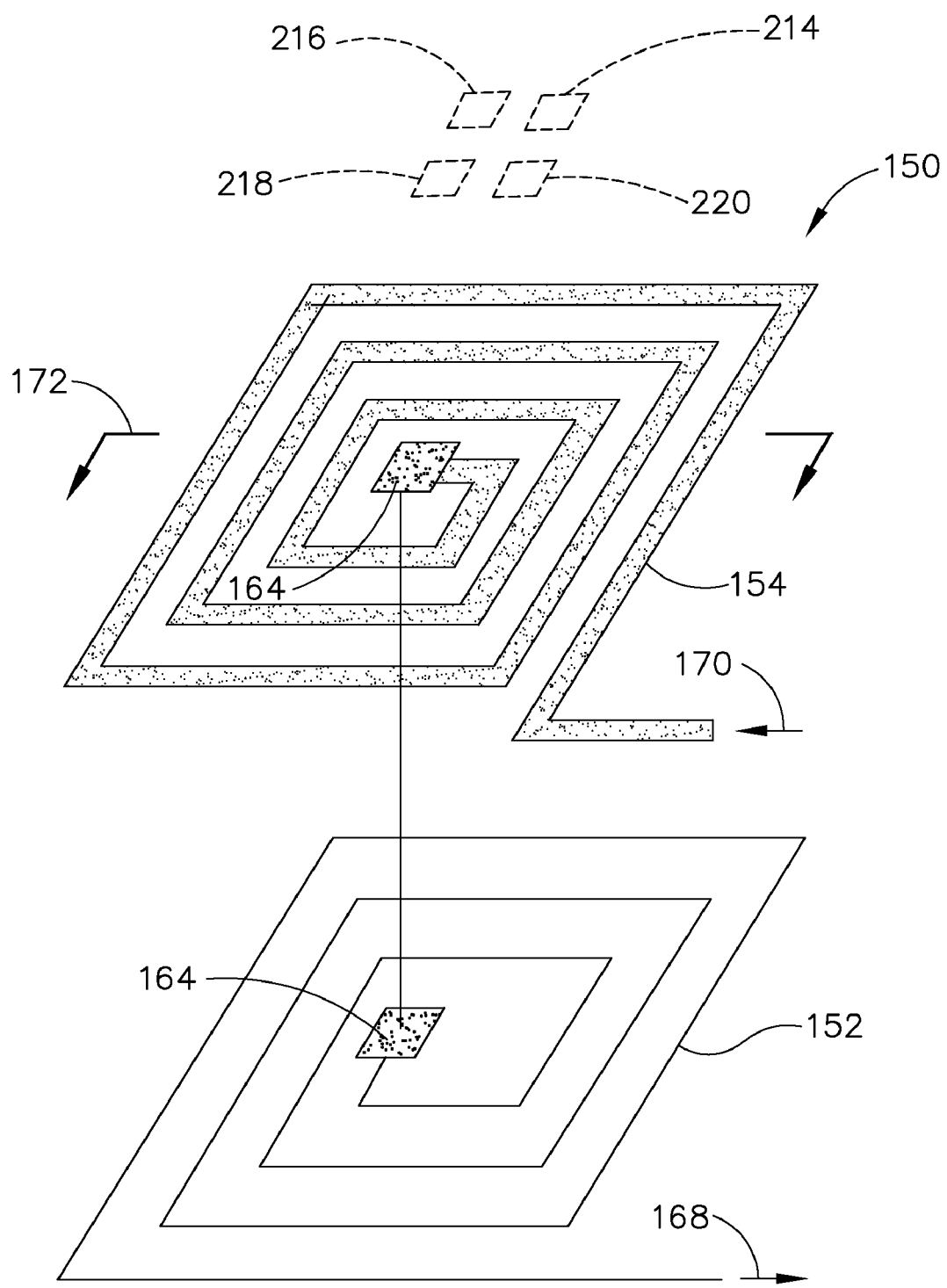
FIG. 4 is a perspective view of the exemplary drive coil of FIG. 3, including bonding pads.
Figure 5:
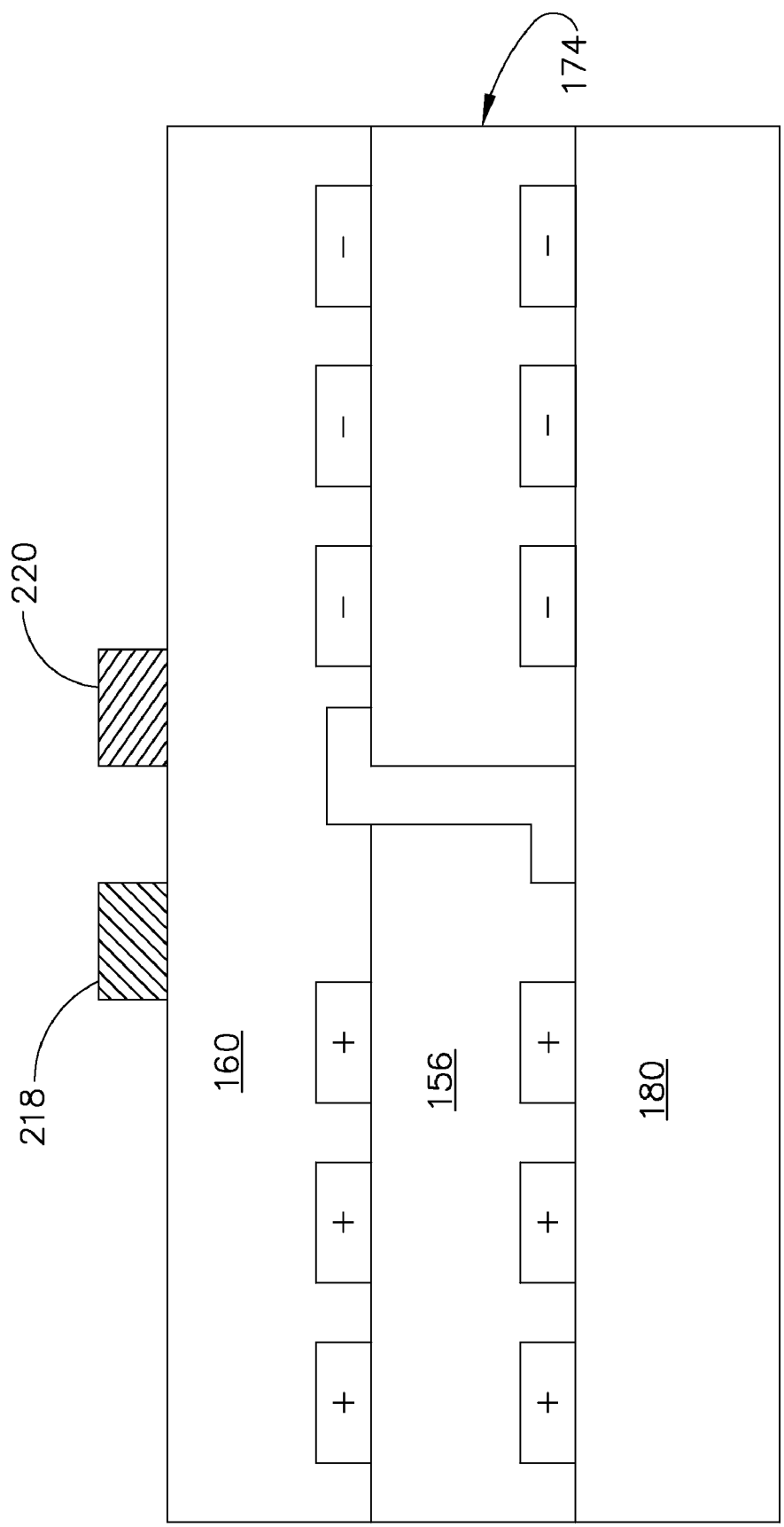
FIG. 5 is a cross-sectional view of the exemplary drive coil of FIG. 3 including bonding pads.

FIGS. 3 and 4 illustrate a top planar and a perspective view of a coil element 150 comprised of two three-turn coil windings 152 and 154, herein also referred to as drive coils 152 and 154, disposed in separate but adjacent layers and centrally connected in a serial manner as a probe element. In the exemplary embodiment, coil windings 152 and 154 are conductive traces, however, coil windings 152 and 154 may be formed from any material that allows coil element 150 to function as described herein. The coil segments of underlying coil winding 152 are disposed as shown in FIG. 5 in a first layer 156 beneath a second layer 160 in which coil 154 is disposed. A square indicates an interlayer electrical connection 164 between respective coils 152 and 154. Arrows 168 and 170 indicate the direction of current flow through coil element 150 at an instant in time. The cross-sectional view of FIG. 5 is taken as indicated at numeral 172 in FIGS. 3 and 4.

FIG. 5 is a cross-sectional view of the structure of FIGS. 3 and 4 taken as indicated at numeral 172. In the exemplary embodiment, coil element 150 includes two layered planar spiral drive coils 152 and 154. However, coil element 150 may include any number of layered planar spiral drive coils including, but not limited to, a single planar spiral drive coil. In one embodiment, drive coils 152 and 154 are copper traces positioned within a flexible material 174. However, drive coils 152 and 154 may be formed from any metallic material. Flexible material 174 includes a plurality of layers of a flexible film, for example, first film layer 156 and second film layer 160. An example of a flexible film is, but is not limited to, a polyimide film. An example of a commercially available polyimide film is Kapton® by DuPont™ of Wilmington, Del. Layering planar drive coils in such an orientation increases the number of coils within a given area. The increased number of coils increases the potential excitation field that can be produced by the eddy current probe. However, increasing the number of layers reduces the flexibility of the drive coil and therefore of the eddy current probe. In the exemplary embodiment, drive coil 152 is positioned at least partially within first film layer 156 and drive coil 154 is positioned within second film layer 160 such that drive coil 154 is opposite drive coil 152. In the exemplary embodiment, first film layer 156 is coupled to second film layer 160 by a layer of adhesive (not shown in FIG. 5). The layer of adhesive may include any known adhesive that facilitates coupling adjacent layers of material together, without adversely affecting the flexibility of coil element 150.

The instantaneous current flow in each cross-sectionally viewed coil segment of FIG. 5 is identified using engineering conventions, "+", indicating current flow into the plane of the page and, ".", indicating current flow out of the plane of the page. Where possible, numerals identifying coil segments have been preserved in FIGS. 3-5 to facilitate cross-sectional visualization of the multilayer fabrication of coil element 150. An exemplary method of fabricating the multilayer flexible coil is a High Density Interconnect (HDI) process. An example of a HDI process is described in U.S. Pat. No. 5,389,876. The HDI process involves patterning coils 152 and 154 onto flexible substrate 180. The HDI process enables reliable fabrication of precise, high-density interconnect eddy current probe arrays quickly, consistently, and in bulk. The multilayer spiral coil can also be fabricated by any other process that enables fabrication of the coils in a flexible substrate. The process involves first patterning coil 152 onto a flexible substrate 180 such as the polyimide Kapton®, as described above, which has been bonded to a support carrier (not shown in FIGS. 3-5). The support carrier may be made of Kovar® steel, to support flexible substrate 180 throughout HDI processing in order to avoid shrinking, wrinkling, etc. Kovar® is a registered trademark of CRS Holdings Inc., a subsidiary of Carpenter Technologies. If desired, substrate 180 may be a ferrite material.

FIGS. 3-5 also illustrate a plurality of bonding pads 214, 216, 218, and 220. Bonding pads 214, 216, 218, and 220 facilitate accurate mounting of a solid-state sensor (shown in FIG. 8) upon coil element 150 as described further below.

Figure 6:
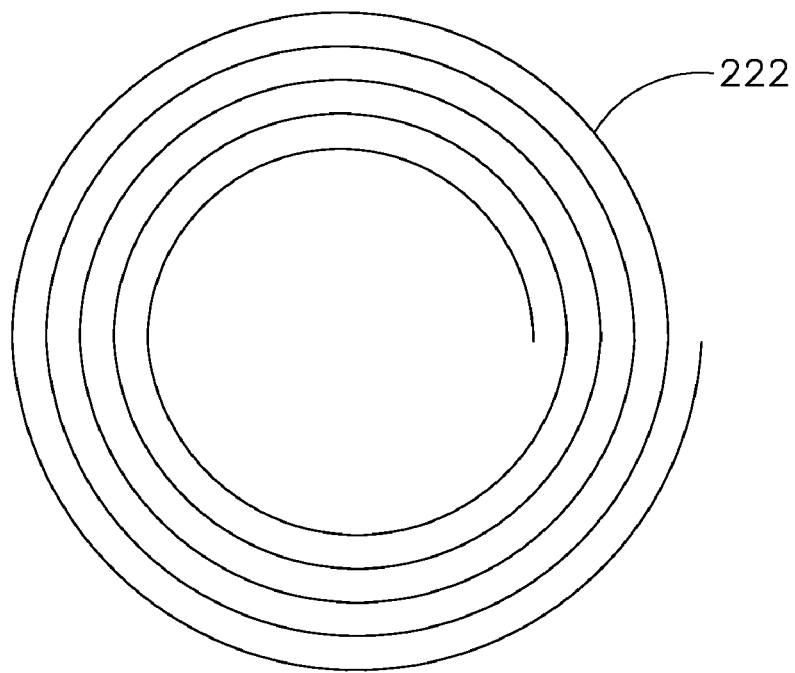
FIG. 6 is a top view of an alternative embodiment of a drive coil.
Figure 7:
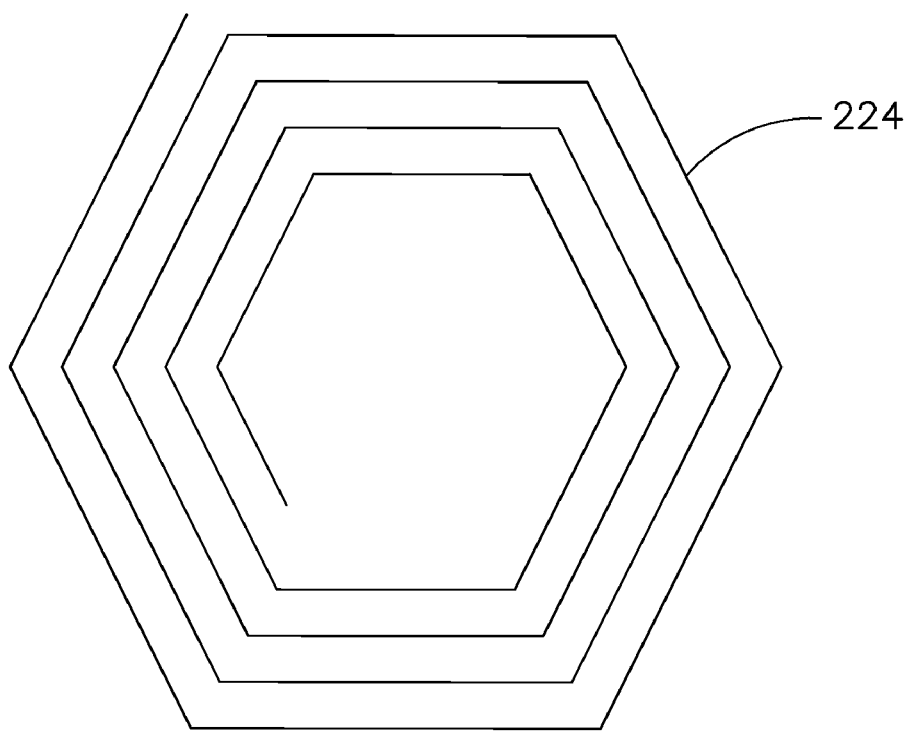
FIG. 7 is a top view of another alternative embodiment of a drive coil.

FIG. 6 is a top view of another exemplary embodiment of a drive coil 222, which is a planar spiral coil having a substantially circular shape. FIG. 7 is a top view of another exemplary embodiment of a drive coil 224, which is a substantially planar spiral coil having a substantially hexagonal shape. The shapes of drive coils 222 and 224 are exemplary only. Planar spiral coils of other shapes may also be included in an eddy current probe as described herein. As described above, the spiral orientation of drive coils 222 and 224 enable a plurality of turns to be formed within a given area. As the number of turns increases within a given area, the excitation field strength that may be produced by the drive coil increases proportionally.

Figure 8:
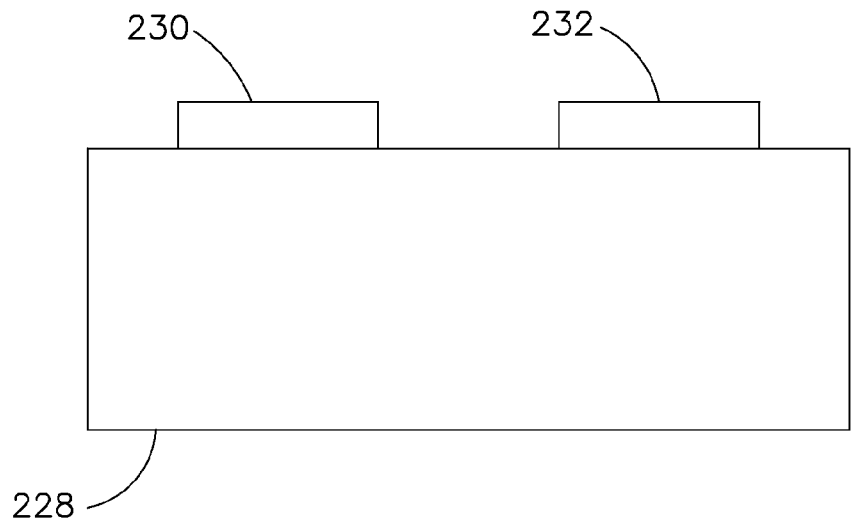
FIG. 8 is a cross-sectional view of an exemplary solid-state magnetic field sensor including bonding pads.
Figure 9:
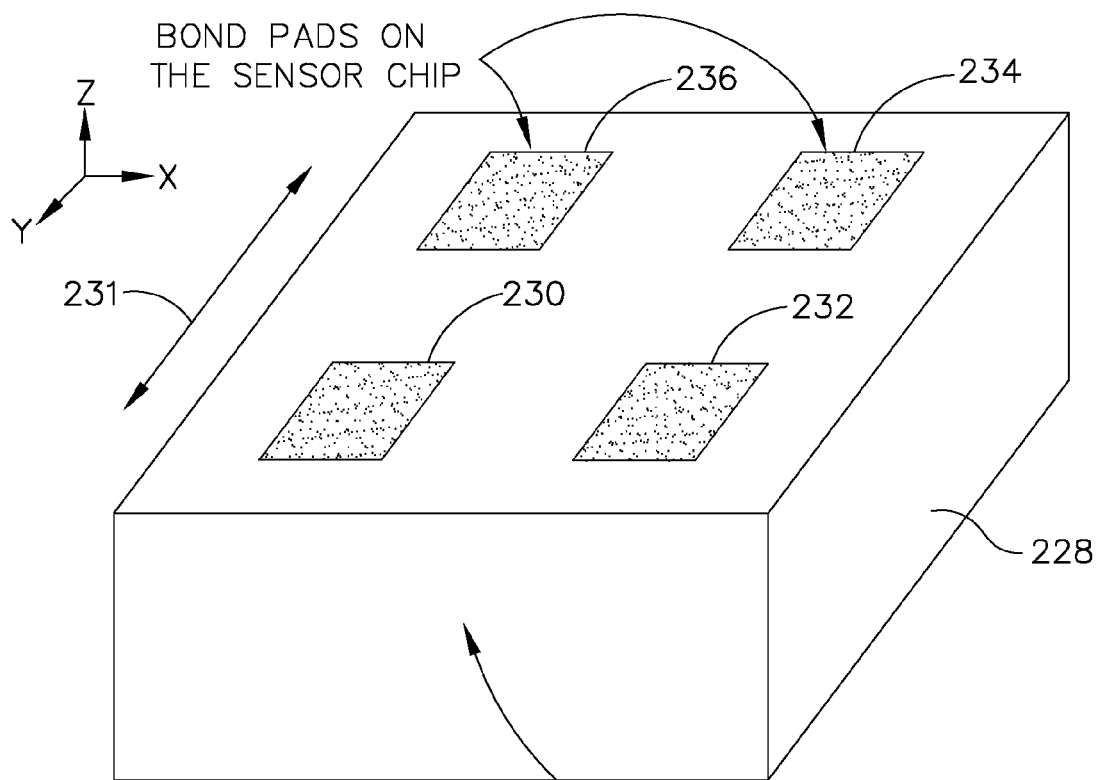
FIG. 9 is a perspective view of the exemplary solid-state sensor of FIG. 8.

FIG. 8 is a cross-sectional view of an exemplary solid-state sensor 228 including a plurality of bonding pads, for example, bonding pads 230 and 232. FIG. 9 is a perspective view of the exemplary solid-state sensor 228 of FIG. 8 including bonding pads 230, 232, 234, and 236. In the exemplary embodiment of FIGS. 8 and 9, solid-state sensor 228 is one of a Hall sensor, an anisotropic magnetic resistor (AMR), a giant magnetic resistor (GMR), a tunneling magnetic resistor (TMR), an extraordinary magnetoresistor (EMR), and a giant magnetoimpedance (GMI). However, solid-state sensor 228 may be any unpackaged solid-state sensor that enables eddy current testing as described herein.

Solid-state sensor 228 is unpackaged, an arrangement also referred to as a die format. A packaged sensor is generally larger than an unpackaged sensor and may negatively affect the flexibility of an eddy current probe. Also, a packaged sensor has a built-in lift-off, which increases the distance from the sensor to the test sample, and thus reduces the probe sensitivity. By using the unpackaged solid-state sensor, distance between the sensor and the drive coil, and the distance between the sensor and the test sample, are minimized.

In the embodiment of FIG. 9, solid-state sensor 228 has a sensitive axis 231 that is parallel to the sensor surface. Coupling sensor 228 to a drive coil, for example, drive coils 152 and 154 of coil element 150 (shown in FIG. 3), accurately at a center of drive coils 152 and 154 minimizes the magnetic field detected by sensor 228 directly from drive coils 152 and 154 which allows sensor 228 to only sense disturbance fields reflected from an abnormality in the test sample.

Figure 10:
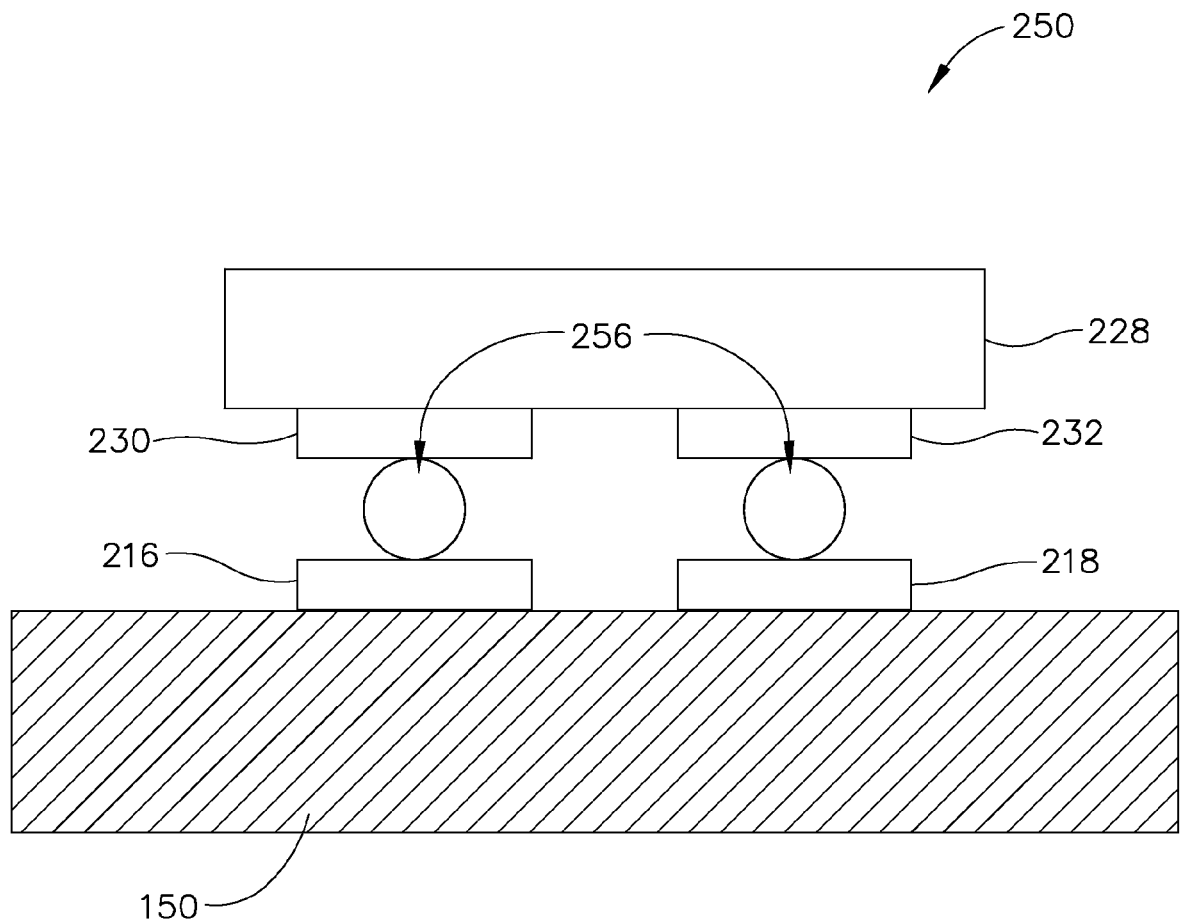
FIG. 10 illustrates an exemplary method of bonding the exemplary solid-state magnetic field sensor of FIG. 8 to the exemplary drive coil of FIG. 3.

FIG. 10 illustrates the exemplary solid-state sensor 228 of FIG. 8 bonded to the exemplary coil element 150 of FIG. 3 to form an eddy current probe 250. Sensor 228 is flipped to align sensor bonding pads 230, 232, 234, and 236 (shown in FIG. 9) to bonding pads 214, 216, 218, and 220 (shown in FIG. 9) on coil element 150. Since bonding pads 214, 216, 218, and 220 are patterned on the coil during the fabrication process described above, by aligning the sensor bonding pads 230, 232, 234, and 236 to coil bonding pads 214, 216, 218, and 220, the position of sensor 228 with respect to coil element 150 is precisely controlled. To form eddy current probe 250, a metal or other bonding material 256 is placed between the bonding pads so that sensor 228 is mechanically attached to the coil center. A flip-chip bonding method, a wire-bonding method, or any other method that enables accurate positioning and bonding of an unpackaged solid-state sensor to a flexible substrate may be used to form eddy current probe 250.

Figure 11:
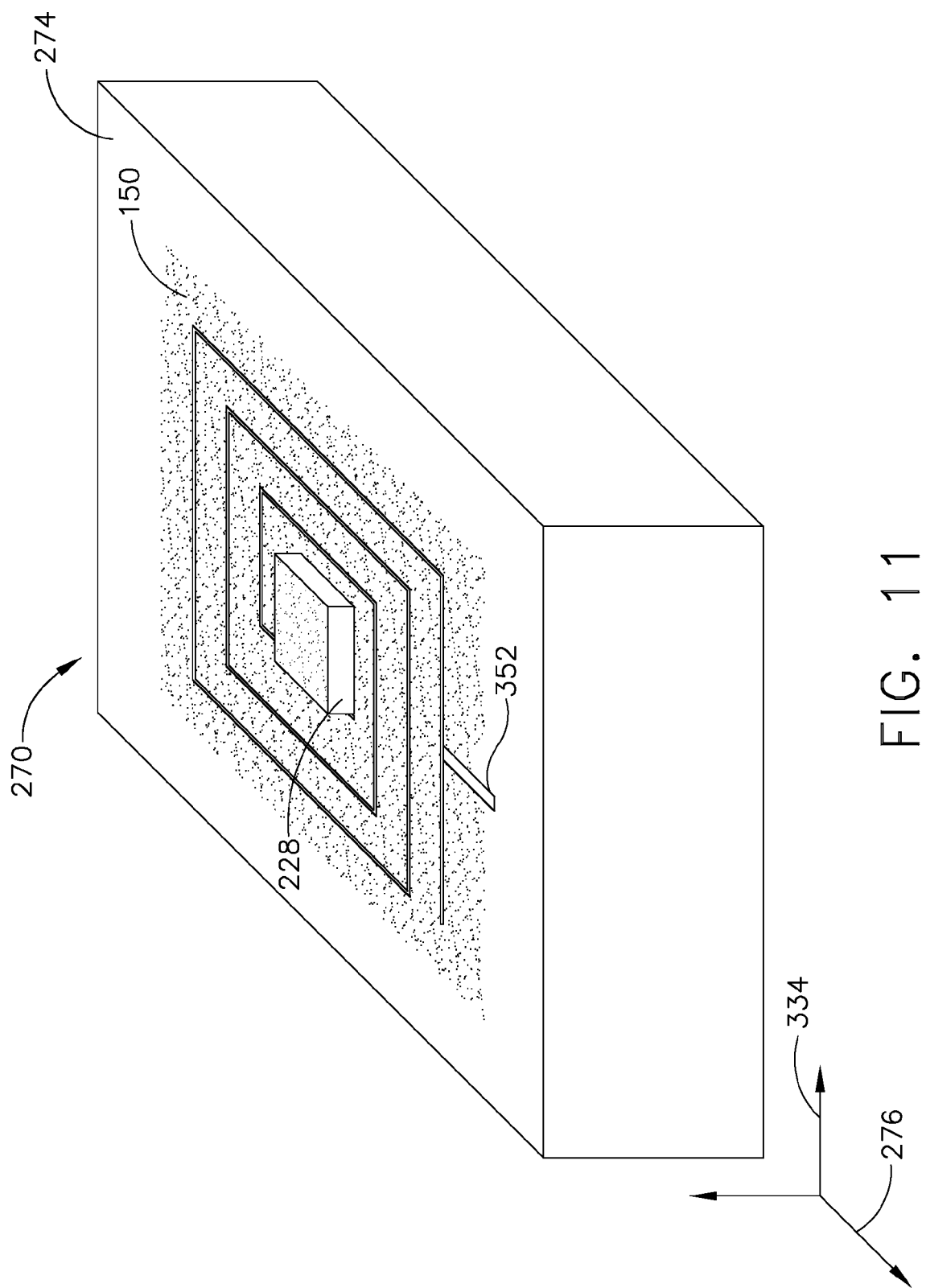
FIG. 11 is a diagram of an exemplary eddy current probe, positioned above a surface to be tested.

FIG. 11 is a diagram of an exemplary eddy current probe 270, positioned above a surface 274 to be tested. Eddy current probe 270 includes at least one flexible drive coil, for example, drive coils 152 and 154 of coil element 150 (shown in FIG. 3). Eddy current probe 270 also includes a solid-state sensor, for example, solid-state sensor 228. The flexibility of coil element 150 enables eddy current probe 270 to flex and more accurately conform to surface 274, and as a result, minimize the lift-off effect.

In operation, coil element 150 is positioned adjacent to the surface 274 to be tested such that coil element 150 is between the surface 274 to be tested and sensor 228. In an alternative embodiment, sensor 228 is positioned adjacent to surface 274 such that sensor 228 is between the surface 274 and coil element 150. In another exemplary embodiment, coil element 150 is formed on a surface of sensor 228.

Figure 12:
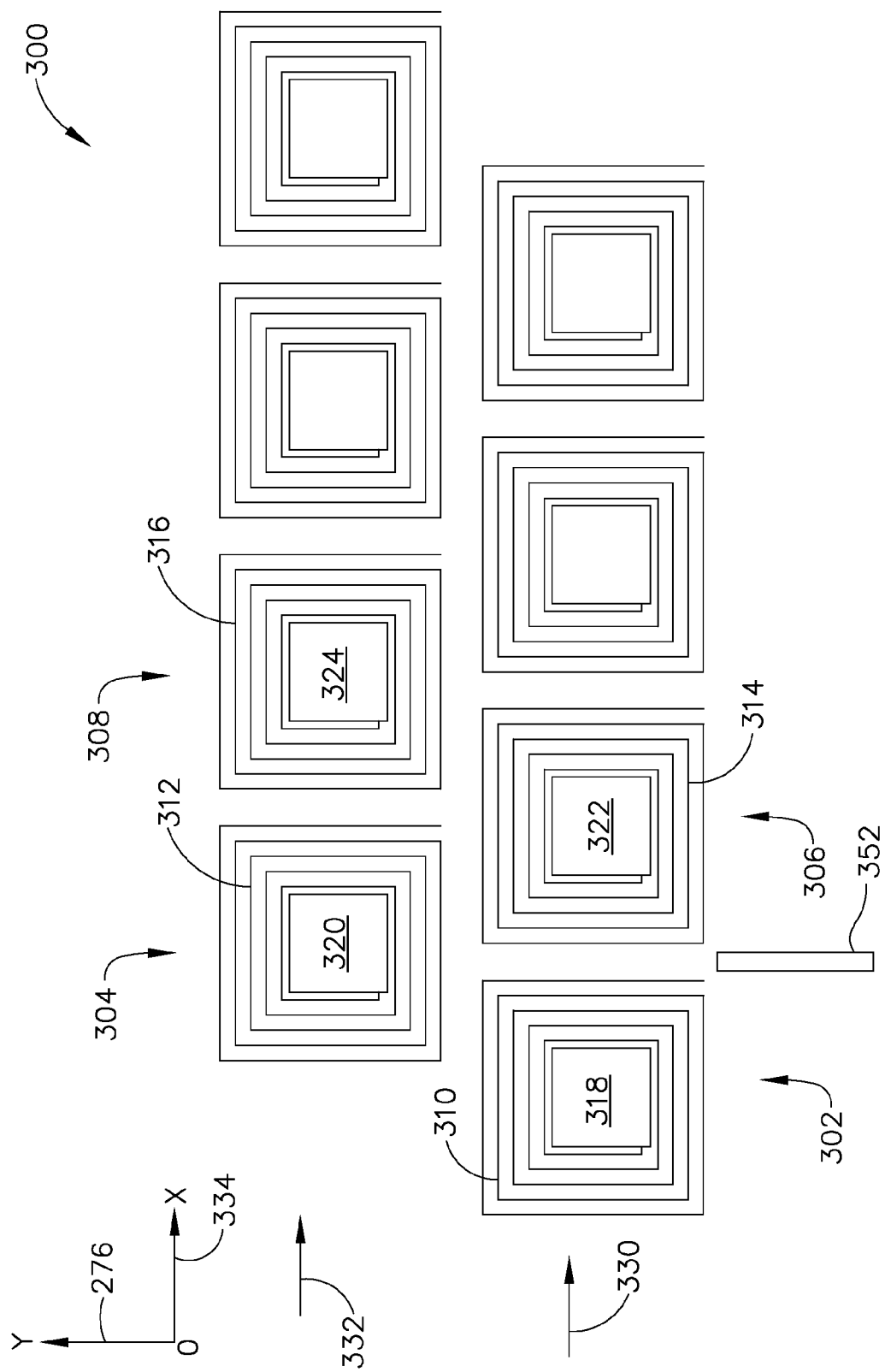
FIG. 12 is a schematic diagram of an exemplary eddy current array probe.
Figure 13:
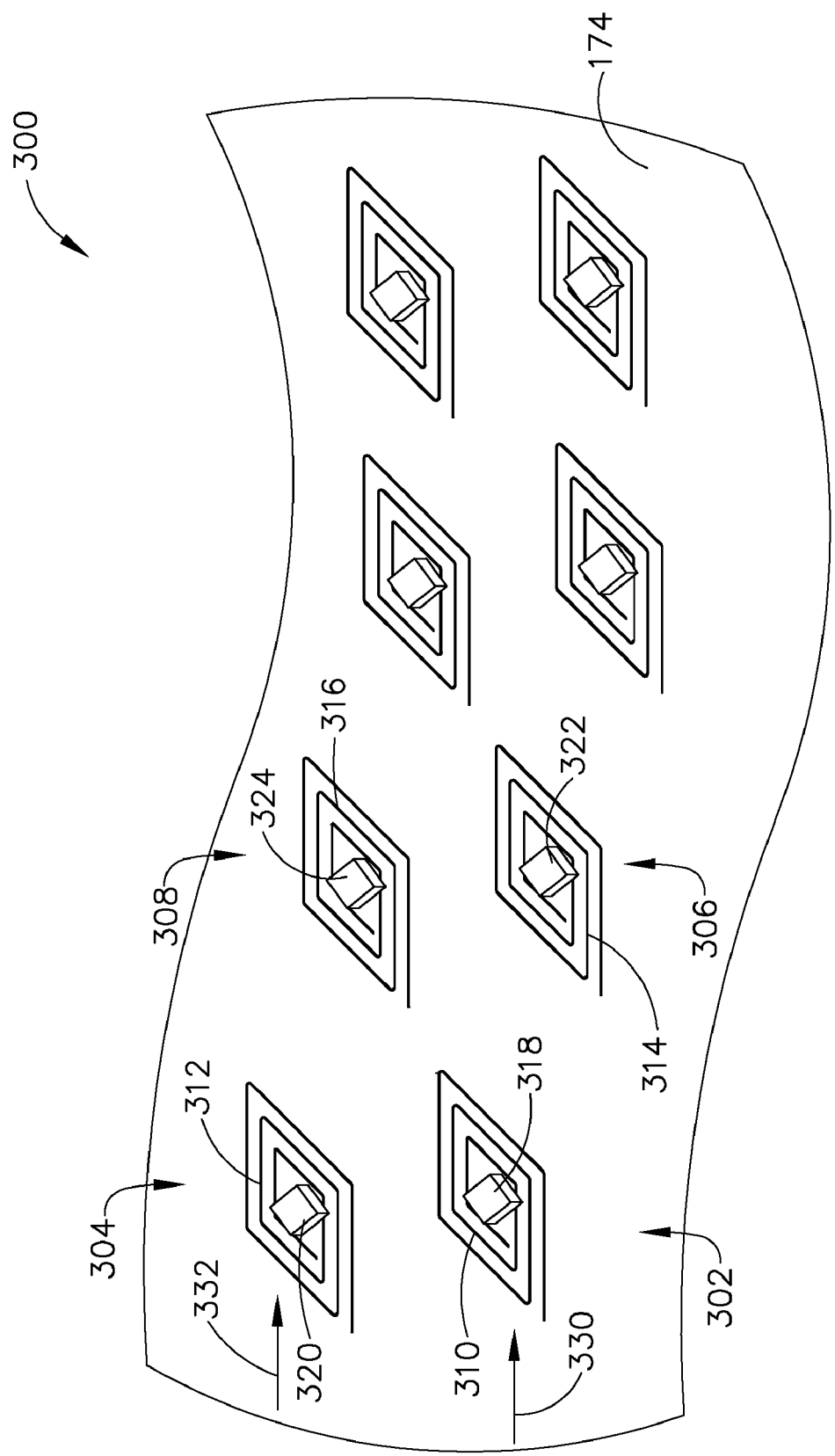
FIG. 13 is a perspective view of the exemplary eddy current array probe of FIG. 12.

FIG. 12 is a schematic diagram of an exemplary eddy current array probe 300. FIG. 13 is a perspective view of the exemplary eddy current array probe 300 of FIG. 12. Eddy current array probe 300 includes a plurality of individual eddy current probes coupled together to form an array. For example, a first eddy current probe 302, a second eddy current probe 304, a third eddy current probe 306, and a fourth eddy current probe 308 are coupled together to define a portion of eddy current array probe 300.

Each individual eddy current probe 302, 304, 306, and 308 includes a coil element, for example, coil elements 310, 312, 314, and 316. As described above with respect to coil element 150 of FIG. 3, coil elements 310, 312, 314, and 316 are positioned within a flexible material 174 and may include multiple drive coils. Eddy current probes 302, 304, 306, and 308 are coupled together via flexible material 174. Flexible material 174 enables eddy current array probe 300 to substantially conform to curved portions of the surface being tested. More specifically, conforming to curved portions of the surface being tested facilitates preventing the lift-off effect even while the multiple probes 302, 304, 306, and 308 of array probe 300 enable testing of a larger area in one pass over a surface than an individual eddy current probe is able to test.

Each individual eddy current probe 302, 304, 306, and 308 also includes a sensor, for example, sensors 318, 320, 322, and 324. Known eddy current probes typically include a drive coil that induces eddy currents in the sample to be tested, and a sensing coil that detects disturbances in the secondary fields indicating flaws in the sample. The sensitivity of a sensing coil is proportional to the number of turns of the sensing coil. However, spatial resolution of a sensing coil decreases as the size of the sensing coil increases. Due to the nature of the sensing coil, there is a trade-off between using a large sensing coil to achieve a desired sensitivity and using a small sensing coil to achieve desired spatial resolution. In contrast to known sensing coils, solid-state sensors can be made relatively small while maintaining sensitivity. In an exemplary embodiment, sensors 318, 320, 322, and 324 may each be a known solid-state sensor, such as, but not limited to, a Hall sensor, an anisotropic magnetic resistor (AMR), a giant magnetic resistor (GMR), a tunneling magnetic resistor (TMR), an extraordinary magnetoresistor (EMR), and a giant magnetoimpedance (GMI). However, solid-state sensors 318, 320, 322, and 324 may be any unpackaged solid-state sensor that enables eddy current testing as described herein. An example of a GMR sensor is a Hitachi GMR sensor by Hitachi of Tokyo, Japan.

In the exemplary embodiment, sensors 318, 320, 322, and 324 are electro-magnetically coupled to respective coil elements 310, 312, 314, and 316. Sensors 318, 320, 322, and 324 may be coupled to coil elements 310, 312, 314, and 316 as described above with respect to FIG. 10.

In the exemplary embodiment, each sensor 318, 320, 322, and 324 is coupled at a center of each respective coil element 310, 312, 314, and 316. The small physical size of die format sensors 318, 320, 322, and 324, in combination with the orientation of the sensors 318, 320, 322, and 324 and the flexibility of material 174, enables eddy current probes 302, 304, 306, and 308 to flex with respect to one another, and also enables each individual eddy current probe 302, 304, 306, and 308 to flex and generally conform to the shape of the surface being tested. In other exemplary embodiments, each of coil elements 310, 312, 314, and/or 316 may not be coupled to an individual sensor. In such an exemplary embodiment, a plurality of coil elements may be coupled to a single sensor.

In the exemplary embodiment, the plurality of individual eddy current probes define two parallel rows 330 and 332. First and third eddy current probes 302 and 306 are aligned substantially co-linearly with respect to one another along an axis 334 and form a portion of first row 330. Second and fourth eddy current probes 304 and 308 are aligned substantially co-linearly with respect to one another along axis 334 and form a portion of second row 332. First row 330 and second row 332 are offset with respect to one another along axis 334 such that the centers of eddy current probes 302 and 306 are substantially aligned with outer edges of eddy current probes 304 and 308.

The staggered orientation of the probes that form first row 330 with respect to the probes that form second row 332 enables eddy current array probe 300 to detect imperfections in a sample being tested anywhere along axis 334. However, eddy current array probe 300 may include any orientation of multiple eddy current probes that enables eddy current array probe 300 to function as described herein. By fabricating the first, second, third, and fourth eddy current probes 302, 304, 306, and 308 to be substantially identical, performance of the first, second, third, and fourth eddy current probes 302, 304, 306, 308 is substantially uniform.

Figure 14:
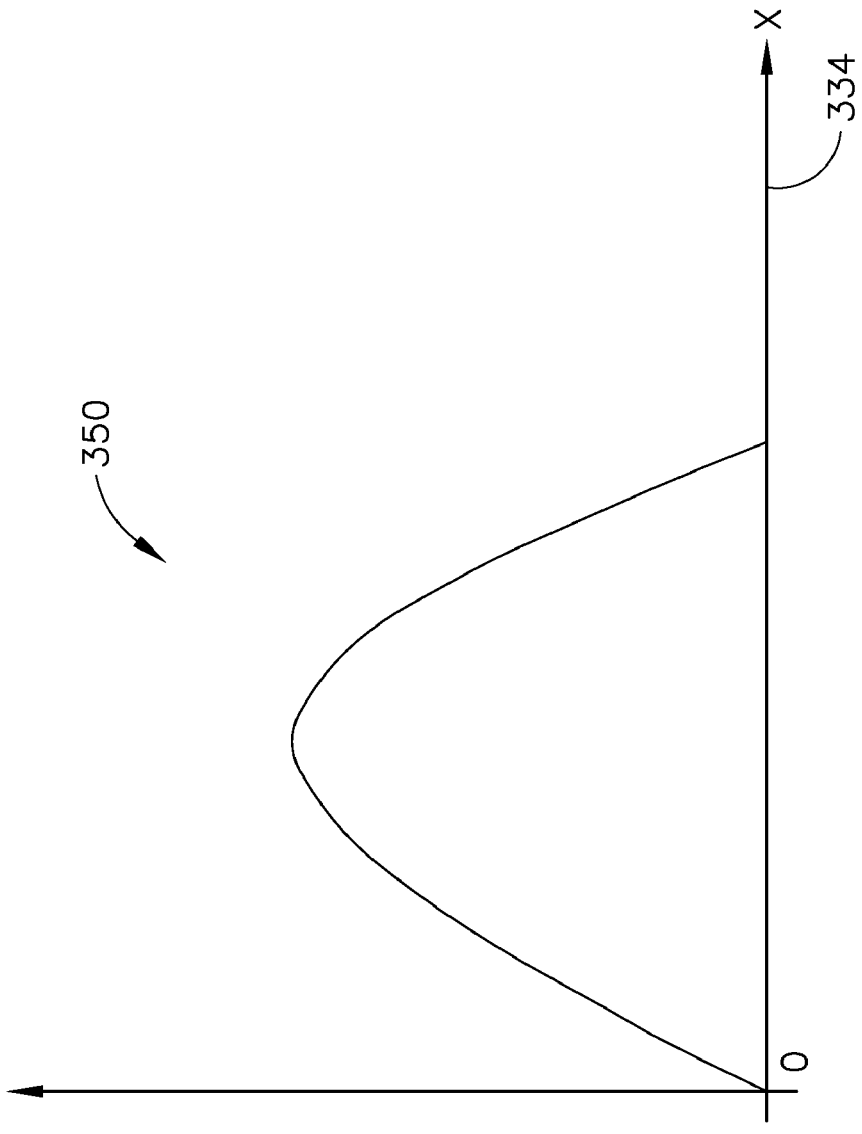
FIG. 14 is a graph of an output of an eddy current probe.

FIG. 14 is a graph 350 of an output magnitude of eddy current probe 270 as compared to a position of an imperfection 352 along an axis 334 relative to the center of eddy current probe 270 (each shown in FIG. 11). As probe 270 is moved along axis 276 (shown in FIG. 11), probe 270 outputs an indication that imperfection 352 has been detected. However, the magnitude of the output is dependent upon the position of imperfection 352 along axis 334 relative to the center of probe 270. The magnitude of the output is a maximum when imperfection 352 is detected under a center of probe 270. The magnitude of the output decreases when imperfection 352 is detected further along axis 334 from the center of probe 270. The orientation of first eddy current probe 302, second eddy current probe 304, and third eddy current probe 306 of eddy current array probe 300 (shown in FIG. 12) enables eddy current array probe 300 to detect imperfections anywhere along axis 334 as eddy current array probe 300 is moved along axis 276.

More specifically, and again referring to FIG. 12, an imperfection 352 may not be detected by first eddy current probe 302 or third eddy current probe 306 if the imperfection is positioned directly between first and third probe 302 and 306 since, as described above, the magnitude of the output of each individual eddy current probe decreases as an imperfection is positioned further along axis 334 from a center of the probe. However, since first row 330 and second row 332 are staggered, should the output of a detected imperfection be low from probe 302, the imperfection will be detected and a higher magnitude output will be produced by second eddy current probe 304.

Figure 15:
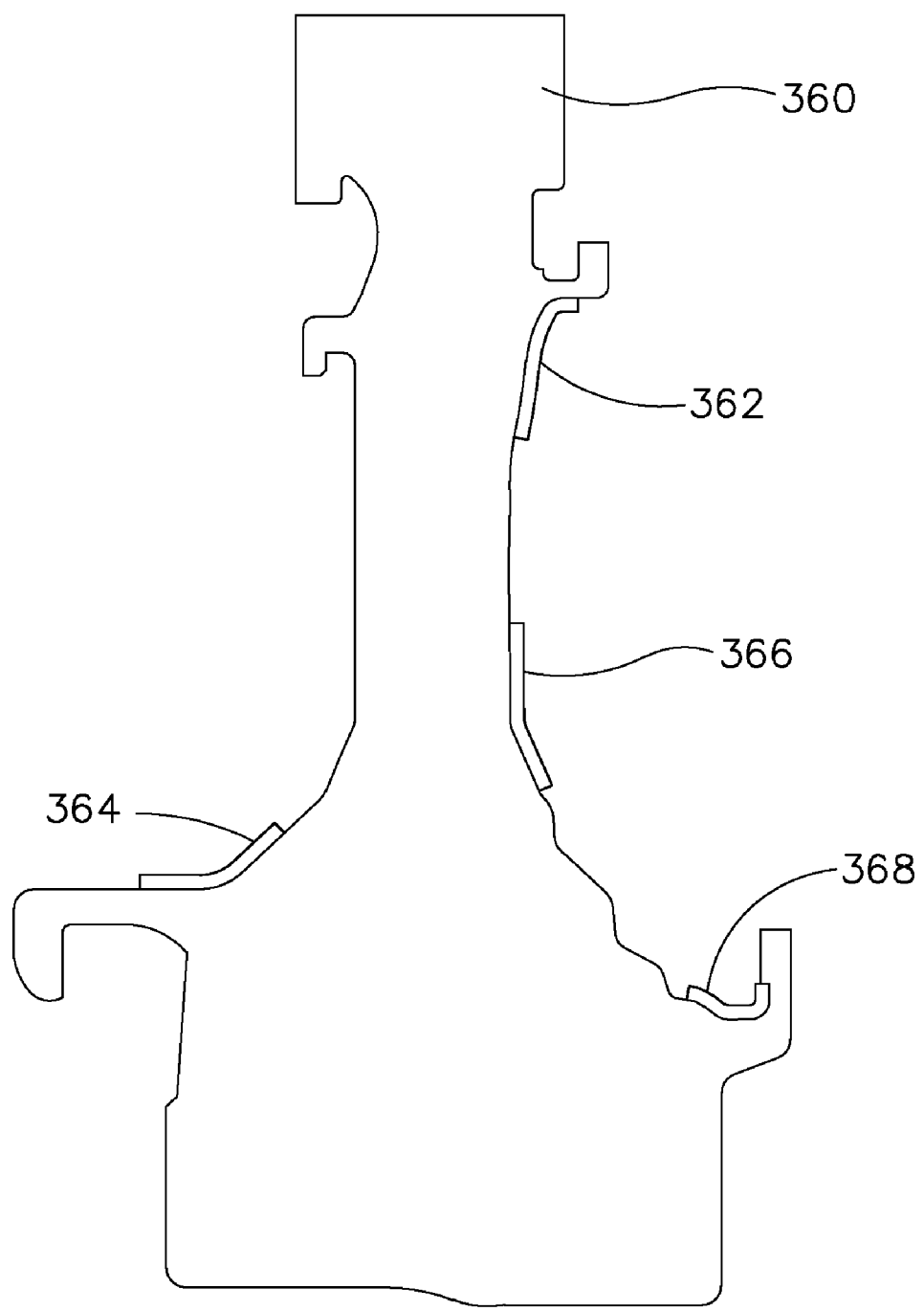
FIG. 15 is a cross-sectional view of a turbine disk.

FIG. 15 is a cross-sectional view of a turbine disk 360 and a plurality of eddy current array probes 362, 364, 366, and 368. In the exemplary embodiment, each of eddy current array probes 362, 364, 366, and 368 is substantially similar to eddy current array probe 300 of FIG. 12. FIG. 15 illustrates eddy current array probes 362, 364, 366, and 368 flexing to conform to the curves of transitional zones included within turbine disk 360. The transitional zones often are subject to stresses that increase the importance of eddy current testing.

The methods described above include orienting a drive coil in a planar spiral in order to efficiently utilize a given area by fitting a large number of windings within the area. Increasing a number of windings is advantageous because increasing the number of windings increases the excitation field that may be produced by the drive coil. Coil elements 310, 312, 314, and 316 are positioned adjacent to, or at least partially within, flexible material 174. Flexible material 174, in combination with the flexibility of coil elements 310, 312, 314, and 316, allows eddy current probes 302, 304, 306, and 308, which make up eddy current array probe 300, to flex with respect to one another and individually flex to conform to the shape of the surface to be tested and minimize the lift-off effect. Unlike known eddy current probes where high spatial resolution is achieved by using a small sensor coil, which negatively affects the sensitivity of the sensor coil, the eddy current probe described above is able to provide high spatial resolution and high sensitivity through the use of a solid-state sensor.

The above-described embodiments of eddy current probes and eddy current array probes provide cost-effective and reliable means for detecting abnormal indications in a component being tested. More specifically, the above-described embodiments describe designing and fabricating individual eddy current probes and also eddy current array probes to facilitate preventing the lift-off effect by enabling flexibility of individual eddy current probes and also of the eddy current array probe. The above-described embodiments of eddy current probes and eddy current array probes also ensure the accurate placement of an unpackaged solid-state sensor at a center of a spiral drive coil. Accurate placement at the center of a spiral drive coil enables the sensor to detect cracks or other abnormalities within the test sample by sensing the disturbed magnetic fields reflected off of the abnormalities and prevents the sensor from directly sensing the magnetic field produced by the drive coil. Furthermore, the alignment of individual eddy current probes within the embodiments of the eddy current array probe described above enables complete coverage of a surface of a test sample by the eddy current array probe.

Exemplary embodiments of eddy current probes and eddy current array probes are described above in detail. The systems are not limited to the specific embodiments described herein, but rather, components of each system may be utilized independently and separately from other components described herein. Each system component can also be used in combination with other system components. More specifically, although the methods and apparatus herein are described with respect to monitor rotating machinery components, it should be appreciated that the methods and apparatus can also be applied to a wide variety of components used within a steam turbine, a nuclear power plant, hydroelectric power dams, or to inspect any rotating machinery components in pressurized liquid applications. Moreover, for example, the drive coils described above may also be used in combination with other systems.

While the invention has been described in terms of various specific embodiments, those skilled in the art will recognize that the invention can be practiced with modification within the spirit and scope of the claims.

What is claimed is:

1. A method of assembling an eddy current probe for use in nondestructive testing of a sample, the eddy current probe including an array of substantially planar drive coil elements and a plurality of unpackaged solid-state magnetic field sensors, the drive coil elements each including at least one drive coil winding, said method comprising:
   positioning the array of substantially planar drive coil elements within a flexible material;
   providing at least one drive coil bonding pad, on the flexible material, for a first drive coil element of the plurality of drive coil elements;
   positioning at least one sensor bonding pad on a first unpackaged solid-state magnetic field sensor of the plurality of unpackaged solid-state magnetic field sensors; and
   coupling the at least one drive coil bonding pad to the at least one sensor bonding pad to couple the first unpackaged solid-state magnetic field sensor to the flexible material, the at least one drive coil bonding pad and the at least one sensor bonding pad configured to align the first unpackaged solid-state magnetic field sensor at a predetermined location with respect to an electromagnetic field created by the first drive coil element.

2. A method according to claim 1 wherein positioning an array of substantially planar drive coil elements further comprises positioning a first drive coil winding within a first layer of the drive coil element and positioning a second drive coil winding within a second layer of the drive coil element, wherein the first drive coil winding is substantially parallel to the second drive coil winding and to the sample during testing.

3. A method according to claim 1 further comprising orienting the plurality of substantially planar drive coil elements in a plurality of linearly aligned rows, wherein the center of each drive coil element in a first row is staggered relative to the center of a corresponding drive coil element in a second row.

4. A method according to claim 1 wherein coupling at least one drive coil bonding pad to the at least one sensor bonding pad to align the first unpackaged solid-state magnetic field sensor at a predetermined location with respect to an electromagnetic field created by the first drive coil element comprises coupling at least one unpackaged solid-state magnetic field sensor to a center of the drive coil element.

5. A method according to claim 1 wherein coupling said first unpackaged solid-state magnetic field sensor to the flexible material comprises coupling the unpackaged solid-state magnetic field sensor to the drive coil element using at least one of a wire-bonding material and a flip-chip mounting method.

6. A method according to claim 1 further comprising fabricating the array of planar drive coil elements using a high density interconnect (HDI) process to pattern the at least one drive coil winding onto the flexible material.

7. A method according to claim 6 wherein fabricating the array of planar drive coil elements further comprises patterning the at least one drive coil bonding pad on the flexible material.

8. An eddy current probe comprising:
an array of substantially planar drive coil elements, the drive coil elements each comprising at least one drive coil winding positioned within a flexible material, said drive coil elements each further comprising at least one drive coil bonding pad; and
an unpackaged solid-state magnetic field sensor comprising at least one sensor bonding pad coupled to said at least one drive coil bonding pad to form the eddy current probe, said at least one drive coil bonding pad and said at least one sensor bonding pad configured to align the unpackaged solid-state magnetic field sensor at a predetermined location with respect to an electromagnetic field created by the drive coil element.

9. An eddy current probe according to claim 8 wherein said at least one drive coil winding is at least one of substantially rectangular, substantially hexagonal, and substantially spiral.

10. An eddy current probe according to claim 8 wherein said flexible material comprises a polyimide film.

11. An eddy current probe according to claim 8 wherein said unpackaged solid-state magnetic field sensor comprises at least one of a Hall sensor, an anisotropic magnetic resistor, a giant magnetic resistor, a tunneling magnetic resistor, an extraordinary magnetoresistor, and a giant magnetoimpedance.

12. An eddy current probe according to claim 8 further comprising at least one of wire-bonding material configured to couple said solid-state sensor to said drive coil element and a bonding material configured to facilitate a flip-chip mounting process.

13. An eddy current probe according to claim 8 wherein said drive coil elements each further comprise a first layer and a second layer, wherein said first layer comprises a first drive coil winding and said second layer comprises a second drive coil winding.

14. An eddy current probe according to claim 8 wherein the predefined location for said solid-state magnetic field sensor with respect to the electromagnetic field is at a center of said drive coil element.

\* \* \* \* \*